United States Patent [19]

Schouteeten et al.

[11] Patent Number: 5,091,566
[45] Date of Patent: Feb. 25, 1992

[54] PROCESS FOR THE MANUFACTURE OF AQUEOUS SOLUTIONS OF GLYOXYLIC ACID

[75] Inventors: Alain Schouteeten, Ezanville; Yani Christidis, Paris, both of France

[73] Assignee: Societe Francaise Hoechst, Puteaux, France

[21] Appl. No.: 374,818

[22] Filed: Jul. 3, 1989

[30] Foreign Application Priority Data

Jul. 1, 1988 [FR] France ................... 88 08957

[51] Int. Cl.$^5$ .................. C07C 59/153; C07C 51/235; C07C 51/27
[52] U.S. Cl. ..................... 562/531; 562/577
[58] Field of Search ................. 562/531, 577

[56] References Cited

U.S. PATENT DOCUMENTS 2,298,387  10/1942  Kenyon et al. ............ 562/531

FOREIGN PATENT DOCUMENTS 0132336  9/1978  Fed. Rep. of Germany ...... 562/531
2001621  2/1979  United Kingdom .

*Primary Examiner*—Vivian Garner
*Attorney, Agent, or Firm*—Browdy and Neimark

[57] ABSTRACT

The invention relates to the preparation of glyoxylic acid by oxidizing an aqueous solution of glyoxal having a pH less than 1 with molecular oxygen in the presence of nitrogen monoxide as a catalyst.

This process allows the practically total conversion of the starting glyoxal with a good yield of glyoxylic acid.

14 Claims, No Drawings

PROCESS FOR THE MANUFACTURE OF AQUEOUS SOLUTIONS OF GLYOXYLIC ACID

The present invention relates to a new process for obtaining aqueous solutions of glyoxylic acid industrially.

Oxidizing aqueous solutions of glyoxal into aqueous solutions of glyoxylic acid by nitric acid, possibly in the presence of either a strong mineral acid such as hydrochloric acid, or of oxalic acid, or of a soluble cobalt salt, or finally, of molecular oxygen, is known. (H. Debus, Annalen, 1857, 102, 28; French Patents Nos. 1,326,605, 2,372,141 and 2,516,506; Federal Republic of Germany Patent Nos. 932,369, 933,987, 1,002,309 and 31,32,006; Japanese Patents No. 73-103,517, 76-29441, 76-80821, 77-105121 and 80-129440).

These processes produce aqueous solutions of glyoxylic acid containing, apart from glyoxal and unchanged nitric acid, relatively large quantities of oxalic acid, and they release large quantities of nitrogen oxides which require expensive absorption means to prevent their being discharged into the atmosphere.

The presence in the aqueous glyoxylic acid solutions of glyoxal and nitric acid is particularly disturbing because of their reactivity with glyoxylic acid. Therefore their elimination has to be carried out quickly and in such a way as to obtain a residual concentration of glyoxal less than 2% in molar proportions with respect to glyoxylic acid and a residual concentration of nitric acid less than 0.05% in molar proportions with respect to the glyoxylic acid. The elimination of the glyoxal from the aqueous solutions of glyoxylic acid is particularly delicate and expensive, because these two products have at least one aldehyde function.

Recently, in the French Patent No. 2,516,506, a process was proposed for the oxidation of aqueous solutions of glyoxylic acid by an oxidizing agent, obtained starting from nitric acid and a strong nonoxidising acid present at a concentration by weight of 6 to 40% in the reactive mixture. In spite of its interest for the weak residual concentrations of nitric acid present in the aqueous solutions of glyoxylic acid obtained, this process, however, does not correspond to commercial requirements because of the high concentrations of unconverted glyoxal.

The Applicant has now discovered a new process for the industrial manufacture of aqueous solutions of glyoxylic acid which avoids these inconveniences.

According to the process of the present invention, aqueous solutions of glyoxylic acid are prepared by reacting, at a pH value less than 1, an aqueous solution of glyoxal with oxygen, in the presence of catalytic quantities of nitrogen monoxide.

As aqueous solutions of glyoxal, there can be used the aqueous solutions of glyoxal available in industry and containing 5 to 40% by weight of glyoxal, advantageously those containing from 10 to 30% of glyoxal and preferably an aqueous solution of glyoxal at 17±3% by weight.

The process according to the invention is carried out at a pH value less than 1. To achieve this pH, the starting aqueous solution of glyoxal is acidified with a strong mineral acid such as hydrochloric acid, sulphuric acid or their mixtures in variable proportions. Advantageously, the aqueous solutions of glyoxal are acidified with 2 moles of hydrochloric acid per liter of solution.

The process according to the invention is carried out by bubbling in molecular oxygen (dioxygen), at a pressure between $10^5$ and $8 \times 10^5$ Pa, advantageously at a pressure of $4 \times 10^5$ Pa. The process is carried out at the most desirable temperature, generally at a temperature between 35° and 75° C., advantageously between 40° and 70° C.

The oxidation catalyst is nitrogen monoxide, NO. Usually between approximately 75 and 150 mmoles of nitrogen monoxide is used per mole of glyoxal used. At the end of the reaction, this catalyst is easily eliminated from the reactive medium by means known per se. In the presence of oxygen, this catalyst oxidizes spontaneously into nitrogen dioxide, $NO_2$, or its dimer, nitrogen tetroxide, $N_2O_4$. On contact with glyoxal, the nitrogen dioxide is reduced to nitrogen monoxide and oxidizes the glyoxal into glyoxylic acid.

The reaction scheme can be written as follows:

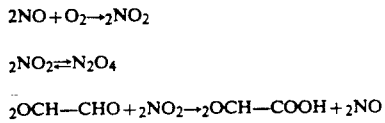

The overall reaction equation is therefore as follows:

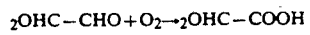

These reactions are quick and exothermic. As a consequence, the reaction temperature has to be kept at the desired level by an appropriate means of heat elimination.

Theoretically, there is no consumption of nitrogen monoxide. However, because of the imperfection of the apparatus and/or certain secondary reactions, from time to time there is a slight consumption of nitrogen monoxide; however this is less than 80 mmoles per mole of glyoxal used, and can be compensated for when the process is carried out continuously, by the addition of the corresponding quantity of fresh nitrogen monoxide.

One of the interesting features of the process of the present invention is that it takes place without dilution of the aqueous solution of glyoxal used.

The process according to the present invention is selective. Therefore, for a transformation rate of 99%. a selectivity of 80±5% is noted, that is to say that at the end of the reaction 80±5% of glyoxal used is recovered in the form of glyoxylic acid. The oxidation of glyoxal either into oxalic acid or into carbon dioxide, is at the most 25% for oxalic acid and 1% for carbon dioxide, expressed in molar proportions with respect to the glyoxylic acid obtained.

In continuous operation, the oxidation reaction can be followed by analysing, by means known per se, the gases evolved, notably oxygen, carbon dioxide, and nitrogen oxides and it can be regulated by adjustment of one or more of its reaction parameters such as temperature, pressure, the rate of introduction of oxygen, and the rate of supply of glyoxal.

The process according to the present invention allows aqueous solutions of glyoxylic acid to be obtained, which are nearly free from nitric acid, and contain, in molar proportions with respect to the glyoxylic acid present, less tan 2.5% glyoxal. Furthermore, very little or no nitrogen oxides are released into the environment.

At the end of the reaction, the oxalic acid possibly present in the aqueous solutions of glyoxylic acid obtained, is eliminated by means known per se. Advantageously it is recovered by the crystallisation of its hydrate with two molecules of water and the final traces are eliminated either by electrodialysis or by treatment with an ion exchange resin, at the same time, if desired, as the elimination of the mineral acid or acids used to acidify the starting aqueous solution of glyoxal to a pH value less than 1. In effect, the mineral acid or acids introduced into the starting solution of glyoxal can be recovered at the end of the reaction by submitting the aqueous solutions of glyoxylic acid obtained either to a treatment by suitably selected ion exchange resins or to a treatment by electrodialysis, well known in other applications. To obtain an aqueous solution having a concentration of glyoxylic acid higher than that which can be obtained directly by the process of the present invention, the aqueous solution of glyoxylic acid can optionally be concentrated by known techniques.

Advantageously, the process of the present invention is carried out continuously, either in a set of agitated reactors, arranged in a series, and equipped with an adequate recycling system for the gases, or in a liquid gas column. The apparatus, kept at the selected temperature and pressure, is supplied continuously with the necessary quantities of oxygen, nitrogen monoxide and glyoxal in aqueous solution, acidified to a pH value of less than 1. The reaction is controlled by the analysis of the gases evolved. On leaving the apparatus, the aqueous solution of glyoxylic acid is cooled to ambient temperature and it is optionally left to crystallise in order to eliminate, if necessary, the oxalic acid present, then, if desired, it is advantageously submitted to an electrodialysis, according to known techniques, in order to obtain on the one hand an aqueous solution of glyoxylic acid free from all other mineral and/or organic acids and on the other hand an aqueous solution of the mineral acid or acids used.

The following examples illustrate the invention without however limiting it.

EXAMPLE 1

By way of a cooled, liquid-gas washing column, the first reactor of a series of three, provided with agitation means and arranged in a series, is fed continuously with an aqueous solution of glyoxal containing 200 g/l of glyoxal (3.446 moles/l) and 73 g/l of hydrogen chloride, with a flow of 50 l/h, that is 172.3 moles/h of glyoxal.

Simultaneously, there is introduced into the first reactor, on the one hand, oxygen, so as to maintain a pressure in the apparatus at $4 \times 10^5$Pa and on the other hand 360 g/h (12 moles/h) of nitrogen monoxide. The temperature is maintained at 45°±3° C. in the first reactor, at 60°±5° C. in the second and at 68°±3° C. in the third. The average time for the reactive solution to stay in the apparatus group is approximately 70 minutes. The gases issuing from the last two reactors are recycled into the first reactor and the latter is in communication with the exterior by way of its liquid gas washing column, provided at the top with a valve adjusted to 4 bars.

On leaving the third reactor, 50 l/h of an aqueous solution of glyoxylic acid is collected, which is colourless, almost without nitric acid and nitrogen oxides and containing 209.5 g/l (2.83 moles/l) of glyoxylic acid, 73 g/l (2 moles/l) of hydrogen chloride, 52.8 g/l (0.58 moles/l) of oxalic acid and 1.75 g/l (30 mmoles/l) of glyoxal. The conversion rate of glyoxal is 99.1% and the selectivity of the reaction as regards glyoxal consumed is 82.8%.

The balance of the reaction as regards glyoxal used is more or less quantitative and the consumption of nitrogen monoxide is approximately 12 moles/h and that of oxygen is approximately 3200 g/h (100 moles/h).

EXAMPLE 2

In a three-necked 2 liter flask fitted with a mechanical agitator, a plunge thermometer, an introduction funnel, an oxygen inlet by a plunge tube fitted with a fritted glass diffuser and a reflux condenser surmounted by a discharge tube bubbling in an aqueous solution of sodium carbonate then in a mercury seal which allows a pressure of $1.225 \times 10^5$Pa to be established in the apparatus, the following is introduced:

1118 g of an aqueous solution containing 174.12 g (3 moles) of glyoxal and 87.6 g (2.4 moles) of hydrogen chloride.

After carefully purging the apparatus with oxygen, this solution is heated under agitation at 45° C.

Then over 15 minutes, while keeping the temperature at 45° C. and regulating the introduction of oxygen so as to avoid any release through the mercury seal, the following is introduced:

7.2 g (0.24 moles) of nitrogen monoxide.

When the introduction is complete, the heating is continued for one hour at 45° C. then for 30 minutes at 55° C. and finally for 30 minutes at 60° C. with gentle bubbling in of oxygen. The oxygen flow is then stopped and the reaction is terminated, keeping the reactive mixture at 60° C. for 30 minutes.

After cooling the reactive mixture to ambient temperature under a slight sweeping of nitrogen, 1173 g of a colourless, aqueous solution is collected, containing:

181.3 g (2.45 moles) of glyoxylic acid,
87.6 g (2.4 moles) of hydrochloric acid,
43.2 g (480 mmoles) of anhydrous oxalic acid,
3.5 g (60 mmoles) of glyoxal,
0.35 g (6 mmoles) of nitric acid.

In the sodium hydroxide trap, 1.2 g (27 mmoles) of carbon dioxide is measured in the form of carbonate.

The conversion rate is 98%, the selectivity is 83.3% for glyoxylic acid and the overall yield of glyoxylic acid is 81.7% of the calculated theory with respect to the glyoxal used. The consumption of oxygen is approximately 54 g.

It goes without saying that the present invention has only been described in a purely explanatory manner and is in no way limiting, and any modification, in particular in technical equivalents can be made without exceeding the scope of the present invention.

We claim:

1. A process for the preparation of an aqueous solution of glyoxylic acid, comprising:
   reacting alyoxal in an aqueous solution with a reactant consisting essentially of molecular oxygen and in the presence of a catalyst consisting essentially of nitrogen monoxide, said catalyst being present in a catalytic amount, and said aqueous solution of glyoxal containing an amount sufficient of a strong mineral acid to provide a pH value less than 1.

2. Process according to claim 1, characterized in that the proportion of nitrogen monoxide is between 75 and 150 millimoles per mole of glyoxal to be oxidized.

3. Process according to claim 2, characterized in that it is carried out under a molecular oxygen pressure of between $10^5$ and $8 \times 10^5$Pa.

4. Process according to claim 2, characterized in that it is carried out at a temperature between 35° and 75°.

5. Process according to claim 1, characterized in that it is carried out under a molecular, oxygen pressure of between $10^5$ and $8 \times 10^5$ Pa.

6. Process according to claim 5, characterized in that it is carried out at a temperature between 35° and 75°.

7. Process according to claim 1, characterized in that it is carried out at a temperature between 35° and 75°.

8. Process according to claim 7, wherein said temperature is between 40° and 70° C.

9. Process according to claim 1, wherein said strong mineral acid is hydrochloric acid.

10. Process according to claim 9, characterized in that the proportion of nitrogen monoxide is between 75 and 150 millimoles per mole of glyoxal to be oxidized.

11. Process according to claim 10, characterized in that it is carried out at a temperature between 35° and 75°.

12. Process according to claim 9, characterized in that it is carried out under a molecular oxygen pressure of between $10^5$ and $8 \times 10^5$ Pa.

13. Process according to claim 12, characterized in that it is carried out at a temperature between 35° and 75°.

14. Process according to claim 9, characterized in that it is carried out at a temperature between 35° and 75°.

* * * * *